United States Patent [19]

Fiato

[11] Patent Number: 5,028,634
[45] Date of Patent: Jul. 2, 1991

[54] TWO STAGE PROCESS FOR HYDROCARBON SYNTHESIS

[75] Inventor: Rocco A. Fiato, Basking Ridge, N.J.

[73] Assignee: Exxon Research & Engineering Company, Florham Park, N.J.

[21] Appl. No.: 397,219

[22] Filed: Aug. 23, 1989

[51] Int. Cl.$^5$ ............................................. C07C 27/00
[52] U.S. Cl. .................................. 518/707; 518/706; 518/715
[58] Field of Search ........................ 518/706, 707, 715

[56] References Cited

U.S. PATENT DOCUMENTS 4,801,573  1/1989  Eri et al. .............................. 518/715

Primary Examiner—Howard T. Mars
Attorney, Agent, or Firm—Jay Simon

[57] ABSTRACT

Hydrocarbon synthesis is carried out in a two stage process wherein the pressure in the first stage is relatively higher and the pressure in the second stage is relatively lower and the second stage catalyst comprises cobalt on alumina.

16 Claims, No Drawings

TWO STAGE PROCESS FOR HYDROCARBON SYNTHESIS

FIELD OF THE INVENTION

This invention relates to a two stage hydrocarbon synthesis process and eliminates the need to drive the initial or first stage reaction to the highest possible conversion. More particularly, this invention relates to a hydrocarbon synthesis process where in a first stage adequate commercial levels of carbon monoxide conversion are obtained and employing in a second, lower pressure stage, a catalyst providing high carbon monoxide conversion at such lower pressures. Still more particularly, the carbon monoxide conversion activity of the second, lower pressure stage is about as high, and preferably higher, than the carbon monoxide conversion activity of the first stage catalyst at second stage pressures.

BACKGROUND

Hydrocarbon synthesis catalysts, also known as Fischer-Tropsch catalysts, have been studied widely and by various researchers in the past sixty years. Preferred processes now usually employ cobalt or ruthenium, cobalt and ruthenium, or promoted cobalt catalysts. The catalysts are supported on a variety of supports, but usually they are supported on inorganic oxides, such as alumina, silica, titania, silicaalumina, and the like.

Promoters can be used to enhance the activity or stability of cobalt or ruthenium catalysts and these promoters may vary. For example, rhenium has been used to promote cobalt catalysts supported on either titania or alumina, see U.S. Pat. No. 4,568,663 and U.S. Pat. No. 4,801,573 respectively. Supported ruthenium catalysts are also quite useful for hydrocarbon synthesis (see U.S. Pat. Nos. 4,477,595; 4,171,320; and 4,042,614). Also, ruthenium and zirconium have been used to promote cobalt supported on silica (see U.S. Pat. Nos. 4,088,671, 4,599,481, and 4,681,867). Two stage hydrocarbon synthesis was disclosed in U.S. Pat. No. 4,443,561 relating to hydrogen:carbon monoxide ratios, but making no differentiation based on the pressure in each reaction stage. Suffice to state that a variety of cobalt containing catalysts have been disclosed for hydrocarbon synthesis processes operating over a relatively wide pressure range. However, to achieve practical results from a hydrocarbon synthesis process, in the sense of converting carbon monoxide and obtaining the maximum availability of desired products, usually $C_5+$ products, these processes are conducted in at least two serially connected stages. That is, with the exception of liquid removal, the second stage operates on the products of the first stage at essentially the outlet pressure of the first stage.

Other two stage hydrocarbon synthesis processes have been reported in the literature. For example, EPA159759, published Oct. 30, 1985 employs a first stage cobalt catalyst and a second stage catalyst having water gas shift activity, while EPA1121.951 published June 27, 1984 employs a second stage catalyst with activity for converting olefinic or oxygenated products to isomeric hydrocarbons. Also, several e.g., U.S. Pat. Nos. 4,547,609, 4,279,830, and 4,159,995 use an iron based first stage catalyst for hydrocarbon synthesis and a second stage catalyst having activity for aromatization. Also, U.S. Pat. No. 4,624,968 employs an iron based first stage catalyst for producing olefins and a second stage catalyst for converting olefins to paraffins with additional CO and hydrogen. All of these systems are based on dual function catalyst systems, that is, where the first stage catalyst is active for a specific chemical reaction and the second stage catalyst is active for a different chemical reaction. However, none of these systems involve a two stage process in which catalysts of essentially equivalent functionality are tailored to the specific operating conditions of each stage.

Hydrocarbon synthesis processes are known to be plagued with several problems. Of these problems, obtaining high conversion and dissipating heat are among the foremost. Since hydrocarbon synthesis is an exothermic reaction, heat must be removed from the reactor to avoid hot spots, catalyst deactivation, and loss of selectivity at higher temperatures. There is usually a preferred temperature range for operating the process which leads to the optimum selectivity to desired higher hydrocarbon products. Lack of efficient heat removal can lead to much higher temperatures in the reactor which, while increasing carbon monoxide conversion, severely debits the selectivity to preferred higher hydrocarbons. At the same time, increasing conversion generates more heat and, thus, a greater burden on heat exchange facilities. Thus, the goals of high conversion and efficient heat transfer tend to oppose each other. To alleviate the problem, lower conversion in a first stage can be accommodated, thereby, reducing the heat load in the first stage. However, this reduced conversion must be made up in the second stage.

Now, increasing pressure for a given reaction and catalyst system generally increases carbon monoxide conversion in hydrocarbon synthesis. However, there is a pressure drop across the first stage reactor and achieving adequate conversion in a second stage can require intermediate compression of the unreacted synthesis gas, an expensive step.

This invention takes advantage of the finding that cobalt on alumina catalysts, specifically cobaltrhenium on alumina is a more active hydrocarbon synthesis catalyst at low pressures than other commonly used catalysts.

SUMMARY OF THE INVENTION

In accordance with this invention, a two stage hydrocarbon synthesis process is provided in which the second stage acts at about the outlet pressure of the first stage and utilizes a non-shifting catalyst that is at least about as active or more active for CO conversion at second stage pressure than the first stage catalyst at second stage reaction pressure.

In hydrocarbon synthesis processes CO conversion activity increases as pressure increases. However, the relative increase in CO conversion with increasing pressure is not the same for every catalyst. Thus, relatively high CO conversion levels are obtained with silica or titania at relatively higher pressures, e.g., above about 10–12 atmospheres, preferably above about 15 atmospheres. The level of CO conversion sets the pressure drop through a reactor. Thus, a 50% CO conversion translate to a 50% drop in total pressure. For example, a 2:1 (approximately stoichiometric) hydrogen:CO mixture at 20 atmospheres and entering a first stage with 60% CO conversion will exit that stage with 2:1 hydrogen:CO at about 8 atmospheres or a 60% drop in pressure (in accordance with Boyle's law). The use of a second stage cobalt containing catalyst, supported primarily on alumina, for second stage conversion makes use of the discovery that at relatively lower pressures, e.g., under about 10-12 atmospheres, cobalt-alumina catalysts are more active for CO conversion than other supported cobalt containing catalysts. Further, because a two stage process is employed, a lower CO conversion level in the first stage can be tolerated and the need for the highest possible CO conversion is obviated. Thus, lower cost catalysts with somewhat reduced CO conversion capability may now be used in the first stage.

This invention is not meant to preclude the use of any particular supported, cobalt or ruthenium containing catalyst in the first stage. While CO conversion activity for cobalt or ruthenium containing catalysts supported by titania or silica may be higher than that for alumina at relatively higher pressures, this increase in activity is on a volumetric basis, that is, moles CO converted per hour per volume of catalyst (cc CO conv/hour/cc cat), and other factors can influence the choice of first stage catalyst, e.g., cost and availability of materials.

By virtue of this invention, the refiner now has much more flexibility in processing schemes because the first stage catalyst need not necessarily be the most active catalyst available, and claims for the most active catalyst vary widely among catalyst and process developers.

The finding that cobalt supported on alumina is more active than other catalysts, particularly cobalt containing catalysts, at lower pressures indicative of second stage pressures, minimizes and preferably eliminates the need for recompression of the feed to the second stage to regain CO conversion activity. Some recompression may be desirable, but in order to achieve the benefits of this invention, the second stage pressure is such that the cobalt/alumina catalyst is of at least equal CO conversion activity and preferably greater CO conversion activity than the first stage catalyst.

In hydrocarbon synthesis reactions, increasing temperature usually increases CO conversion activity for a given catalyst, but can be disadvantageous relative to product selectivity. That is, increasing temperature to increase conversion may lead to increased amounts of methane or carbon dioxide which are undesirable products.

Consequently, a balance must be struck between productivity and selectivity. Because hydrocarbon synthesis is a highly exothermic process and cooling is required to prevent excessive temperatures, the second stage reaction is usually at or about the same temperature as the first stage reaction, although the temperature in each stage may be different depending on the refiner's needs.

Aluminas come in a variety of different phases and virtually every phase is useful in some form of catalysis. The surface area of alumina may vary from a few square meters per gram, e.g., 1-2 $m^2$/gm (BET), for alpha aluminas, and up to 500-600 $m^2$/gm or higher (BET) for eta or gamma aluminas. For hydrocarbon synthesis, higher surface area aluminas, such as gamma alumina, are preferred. Because this material has such a high surface area relative to rutile phase titania, considerably more cobalt can be deposited on to alumina than on to titania, a greater number of cobalt sites can be achieved, and the cobalt dispersion is increased. That is, with the higher surface area material there is less tendency for one crystal of cobalt to fall on another crystal of cobalt resulting in little or no increase in dispersion even though the amount of cobalt is increased. For example, the cobalt loading on a titania support may range from about 5-25 wt%, preferably 10-25 wt% and excellent CO conversion will be obtained. However, the cobalt loading on an alumina support may range from about 5-60 wt%, preferably 5-45 wt%; see, for example, U.S. Pat. No. 4,801,573. Thus, by increasing the cobalt loading, a suitable cobalt-alumina catalyst having adequate CO conversion activity for a first stage reaction may be produced.

First stage reaction conditions include temperatures ranging from about 160° C. to about 290° C., preferably about 190° C.-260° C., more preferably about 190° C.-230° C. While pressures may range from about atmospheric to about 600 psig, first stage pressures generally range from about 150 psig to about 400 psig. Hydrogen to CO ratios may range from about 0.5:1 to about 4:1, preferably about 1.7:1 to 2.5:1, and most preferably at or slightly below stoichiometric the stoichiometric ratio being about 2.1:1. Space velocity for fixed bed reactors may range from about 100 v/v/hr to 10000 v/v/hr, preferably 300 v/v/hr to 5000 v/v/hr.

Second stage reaction conditions will be similar to first stage conditions except that pressures will be reduced by the level of conversion in the first stage and pressure drops of 40%-70% corresponding to 40-70% conversion through the first stage are not uncommon. Preferred conversion levels in the first stage are at least about 50%, preferably about 50-70%, preferably 60-70% with concomitant reductions in pressure. There may be some need for hydrogen or carbon monoxide make up, and this can be accomplished easily.

The products of the first stage comprise $C_{2}+$, preferably $C_{5}+$ hydrocarbons, methane, water, carbon dioxide and unconverted synthesis gas, hydrogen and carbon monoxide. At reactor outlet conditions, some of the product will condense, simply because of the pressure drop across the reactor, and that product is removed from the stream entering the second reaction stage. It may or may not be desirable to cause condensation and removal of product, but it is preferable to remove that much of the product that is liquid at first stage outlet conditions.

In a preferred method of operation the hydrogen:carbon monoxide ratio in each stage is at or slightly below the stoichiometric ratio, that is, from about 1.7:1 to about 2.1:1. Operation at slightly below the stoichiometric ratio in the first stage will result in a slightly lower hydrogen:carbon monoxide ratio in the second stage, absent make-up hydrogen. This operation is preferred in order to retain some CO partial pressure exiting the second stage. Thus, if the hydrogen:carbon monoxide ratio is above about 2.1:1 in the first stage and no make up carbon monoxide is used, the second stage will use up all of the remaining carbon monoxide leading to catalyst deactivation and process instability. Regardless of the operating conditions, the, the outlet of the second stage should have at least about 0.5 atmospheres CO partial pressure, preferably at least about 0.7 atmospheres CO partial pressure.

The first stage catalyst can be any catalyst that provides adequate CO conversion activity at the pressures utilized in the first stage; that is, relatively higher pressure, e.g., above about 10-12 atmospheres. The supported catalyst contains cobalt or ruthenium as the active metal and is preferably a cobalt containing catalyst. That is, the catalyst may contain cobalt or cobalt and ruthenium.

Ruthenium, when used as the primary catalytic metal is present on amounts ranging from about 0.5 to 5.0 wt%. When used in conjunction with cobalt, small amounts of ruthenium are adequate to promote catalyst activity, e.g., weight ratios of 0.1:1 up to 1:1.

Suitable support materials are those inorganic oxides used for catalyst supports and, for example, reported in U.S. Pat. Nos. 4,171,320 and 4,042,614, and generally Group IVB or Group VB metal oxides, and alumina. Preferred materials are alumina, silicaalumina, silica and titania, or supports containing these materials primarily. Specifically preferred are titania and alumina supports or supports containing primarily titania or alumina, that is, at least 50 wt% titania or alumina, preferably at least 70 wt% titania or alumina, and titania preferably 80%+titania. When titania is employed, the rutile phase is most preferred, and the rutile:anatase ratio is at least 2:3, preferably at least 3:2, more preferably at least 4:1. The rutile/anatase ratio is determined by ASTM D 3720-78: Standard Test Method for Ratio of Anatase to Rutile in Titanium Dioxide Pigments by Use of X-Ray Diffraction. Titania can also be used with other oxides, such as alumina, zirconia, and silica in amounts ranging from about 0.1 wt% to about 20 wt%, preferably 0.5 to 10 wt%, most preferably 1 to 5 wt%.

Promoter metals may also be used, such as zirconium, titanium, rhenium, cerium, hafnium, and uranium. Hafnimum, rhenium, and cerium are preferred, titania supports and rhenium is particularly preferred for promoting cobalt on titania and alumina supports. When promoter metals are used, the ratio of promoter to primary catalytic metal, e.g., cobalt or ruthenium, is at least about 0.05:1, preferably at least about 0.1:1 to 1:1. Rhenium has been shown to enhance the activity of cobalt on titania, ruthenium on titania, and cobalt on alumina; see U.S. Pat. Nos. 4,568,663, 4,558,030, and 4,801,573, respectively. Any of these catalyst are suitable first stage catalysts.

The second stage catalyst is an alumina supported, cobalt containing catalyst. The support is primarily alumina, and preferably essentially all alumina. The catalytic metal is cobalt, in amounts previously mentioned, and may also contain a rhenium promoter. At second stage total pressures, which can be at most 40%, usually about 50–60% of the first stage total pressure, cobalt on alumina has superior CO conversion activity relative to non-alumina supported catalysts (that is, catalysts that contain at least 50% of another support material, e.g., titania).

Alumina support materials may also incorporate oxides of the actinides and lanthanides. These oxides are known to provide stability and increased hydrocarbon yields in Fischer-Tropsch processes. The use of these materials is reported in U.S. Pat. Nos. 4,399,234, 4,605,680, and 4,801,573. Suitable oxides are, for example $Sc_2O_3$, $Y_2O_3$, $Ac_2O_3$, $Pr_2O_3$, $PrO_2$, $Nd_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, $Lm_2O_3$, $UO_2$, $UO_3$, $U_3O_8$, $UO_4.2H_2O$, and the like. Preferred materials are $Th_2O_3$, $La_2O_3$, $Ce_2O_2$, $ZrO_2$, $HfO_2$, and unseparated rare earth mixtures high in lanthanium, praseodynium, and neodymium. The most preferred is thoria. These materials are used in amounts of 0.1 to about 10 wt%, preferably about 0.5 to 5.0 wt%.

Thus, the invention makes use of the finding that cobalt on alumina is more active for CO conversion at lower pressures, e.g., up to up about 10–12 atmospheres, than other catalysts, particularly cobalt containing catalysts, and that at higher pressures, e.g., above about 10-12 atmospheres any one of several catalysts may be adequate, for any one of several reasons. This finding is based on comparisons at constant temperature, since temperature can effect CO conversion activity.

Catalyst preparation is in accordance with well-known techniques described in earlier mentioned patents and other relevant literature. The procedures given hereinbelow are illustrative.

The catalytically active metal, or metals, preferably cobalt or cobalt promoted rhenium, can be dispersed upon a calcined support in a manner which will distribute the metal, or metals, essentially uniformly throughout the particles from the center outwardly, or essentially upon the peripheral surface of the particle, preferably the latter when fixed bed processes are employed. In distributing the metal, or metals, uniformly throughout the support particles, e.g., the metal, or metals, can be deposited on the support particles from solution in preselected amounts to provide the desired absolute amounts, and weight ratio of the respective metal, or metals. Suitably, e.g., cobalt, or cobalt and rhenium, are composited with the support by contacting the support with a solution of a cobalt-containing compound, or salt, or a rhenium-containing compound, or salt, followed by impregnation of the other component. Optionally, the cobalt, or cobalt and rhenium can be co-impregnated upon the support. The cobalt used in the impregnation can be any organometallic or inorganic compound which decomposes to give cobalt oxides upon calcination, or can be directly reduced to cobalt in flowing hydrogen, such as cobalt nitrate, acetate, acetylacetonate, naphthenate, carbonyl, or the like, the nitrate being preferred. Likewise the rhenium compound used in the impregnation can be any organometallic or inorganic compound which decomposes to give rhenium oxides upon calcination, or rhenium upon reduction, e.g., perrhenic acid, ammonium perrhenate and the like. The amount of impregnation solution used should be sufficient to completely immerse the carrier, usually within the range from about 1 to 20 times of the carrier by volume, depending on the metal, or metals, concentration in the impregnation solution. The impregnation treatment can be carried out under a wide range of conditions including ambient or elevated temperatures. On the other hand, the catalytically active cobalt component is most preferably dispersed and supported upon the peripheral surface of the support as a thin catalytically active surface layer, or film, ranging in average thickness from about 20 microns to about 250 microns, preferably from about 40 microns to about 200 microns, with the loading of the cobalt expressed as the weight metallic cobalt per packed bulk volume of catalyst ranging from about 0.03 grams (g) per cubic centimeter (cc) to about 0.15 g/cc, preferably from about 0.04 g/cc to about 0.09 g/cc catalyst. The feature of a high cobalt metal loading in a thin catalytically active layer located at the surface of the particles can optimize the activity, selectivity and productivity of the catalyst in producing liquid hydrocarbons from synthesis gas, while minimizing methane formation in fixed bed reactors.

The surface impregnated catalysts can be prepared by spray techniques where a dilute solution of a cobalt compound, alone or in admixture with a promoter metal compound, or compounds, as a spray is repetitively contacted with hot support particles. The particulate support particles are maintained at temperatures equal to or above about 140° C. when contacted with the spray, and suitably the temperature of the support particles ranges from about 140° C. up to the decomposition temperature of the cobalt compound, or compounds in admixture therewith; preferably from about 140° C. to about 190° C. The cobalt compound employed in the solution can be any organometallic or inorganic compound which decomposes to give cobalt oxide upon initial contact or upon calcination, such as cobalt nitrate, cobalt acetate, cobalt acet:ylacetonate, cobalt naphthenate, cobalt carbonyl, or the like. Cobalt nitrate is especially preferred while cobalt halide and sulfate salts should generally be avoided. The cobalt salts may be dissolved in a suitable solvent, e.g., water, organic or hydrocarbon solvent such as acetone, methanol, pentane or the like. The total amount of solution used should be sufficient to supply the proper catalyst loading, with the film being built up by repetitive contacts between the support and the solvent. The preferred catalyst is one which comprises cobalt, or cobalt and promoter, dispersed upon the support. Suitably, the support particles are contacted with a spray which contains from about 0.05 g/ml to about 0.25 g/ml, preferably from about 0.10 g/ml to about 0.20 g/ml, of the cobalt compound or cobalt compound plus the compound containing the promoter metal, generally from at least about 3 to about 12 contacts, preferably from about 5 to about 8 contacts, with intervening drying and calcination steps being required to form surface films of the required thicknesses. The hot support particles, in other words, are spray-contacted in a first cycle which includes the spray contact oer se with subsequent drying and calcination, a second cycle which includes per se with subsequent drying and calcination, etc., to form a film of the required thickness and composition. The drying steps are generally conducted at temperatures ranging above about 20° C., preferably from about 20° C. to about 125° C., and the calcination steps at temperatures ranging above about 150 C, preferably from about 150° C. to about 500° C.

Alternatively, cobalt and ruthenium with or without promoters may be impregnated onto the support by immersing the support in appropriate solutions as described above and in relevant references known to the art.

In preparing catalyst some care need be exercised to insure that the catalyst supports are treated appropriately. That is, they must be adequately inert and strong enough to withstand reaction conditions, and they must not be treated in a manner as to detract from their catalytic activity. For example, reducing the metal salts or oxides to the elemental metal on an alumina support conditions should be in the area of about 350° C.-500° C. for about 10 hours, while titania is better treated at temperatures of about 200°-400 ° C. for 2-5 hours. For more information on proper support treatment, see C. Bartholomew, R. Reuel, Ind. Eng. Chem. Prod. Res. Dev. 24, 56 (1985).

The following examples illustrate this invention.

Example 1 - Comparative Performance of $Al_2O_3$ and $TiO_2$ Supported Cobalt at 1 atmosphere.

These examples are shown in European Patent Application 0 313 375, published Apr. 26, 1989.

| Catalyst | % CO Conversion |
|---|---|
| 12% $Co/Al_2O_3$ | 12 |
| 12% $Co/TiO_2$* | 11 |
| 12% $Co/TiO_2$** | 11 |

*Support Calcined at 500° C.
**Support Calcined at 600° C.

Conditions: $H_2$ pretreatment 1° C./minute to 350° C., hold for 10 hours, 2/1 $H_2$/CO, 1680 $cm^3$/g cat/hr feed rate, 10–30 hour on stream time.

This example shows a slight advantage for $Co/Al_2O_3$ relative to $Co/TiO_2$ at low pressures.

Example 2 - Comparative performance of $Al_2O_3$ and $TiO_2$ Supported Cobalt at 1 atmosphere These examples are shown in Vannice, M.A., J. Catalysis, 74, 199–202, p. (1982).

| Catalyst | $\mu$mol CO/g Cobalt/sec |
|---|---|
| 2% $Co/Al_2O_3$ | 20 |
| 1.5% $Co/TiO_2$ | 13 |

Conditions: $H_2$ pretreatment at 450° C. for 1 hour, 3/1 $H_2$/CO, <1 hour on stream time.

Again, a slight advantage for $Co/Al_2O_3$ is shown relative to $Co/TiO_2$.

Example 3 - Comparative Performance of $Al_2O_3$ and $TiO_2$ Supported Cobalt at 1 atmosphere These examples are taken from Niiyama, H., Pan-Pacific Synfuels Conf., B-11 (1982).

| Catalyst | % CO Conversion |
|---|---|
| 5% $Co/Al_2O_3$ | 5.6 |
| 5% $Co/TiO_2$ | 3.4 |

Conditions: $H_2$ pretreatment at 400° C. for 1 hour, 3/1 $H_2$/CO, 234° C. reaction temperature, 2–3 hours on stream time.

These examples show a substantial advantage for $Co/Al_2O_3$ relative to $Co/TiO_2$ because sufficient amounts of metal are now used to promote the hydrocarbon synthesis reaction.

Example 4 - Comparative Performance of $Al_2O_3$ and $TiO_2$ Supported Cobalt at 1 atmosphere These examples are taken from Reuel, R. and Bartholomew, C., J. Catalysis, 85, 78-88, p. (1984).

| Catalyst | $H_2$ Pretreatment Temp (°C.) | Time (Hr) | Nco ($\times 10^2$) | % D | Activity (N × D) |
|---|---|---|---|---|---|
| 10% $Co/Al_2O_3$ | 375 | 20 | 1.3 | 9.9 | 12.9 |
|  | 525 | 2 | 6.4 | 6.7 | 42.9 |
| 10% $Co/TiO_2$ | 400 | 16 | 4.1 | 4.5 | 18.5 |
|  | 525 | 2 | N/A | 2.3 | N/A |

Conditions: 2/1 H2/CO, 500–2000 SHSV feed rate, 175°–225° C. reaction temperature, 20+ hours on stream time.

Example 5 - Comparative performance of SiO$_2$, Al$_2$O$_3$ and TiO$_2$ at 5.6 atmospheres Cobalt/alumina and cobalt/titania catalysts were prepared by the incipient wetness technique using aqueous acetone on methanol cobalt nitrate solutions. The surface areas were silica - 280 m2/gm, alumina - 180 m2/gm, and titania (60% rutile) - 10 to 20 m2/gm. The salt was decomposed in oxygen and reduced in flowing hydrogen until all of the metal was reduced. Samples were taken after achieving steady state, >24 hours on stream, from a fixed bed reactor at 200 ° C., 2/1 hydrogen:Co, 5.16 atmospheres.

| Catalyst | Activity, Moles CO Converted g-atom CO/Hour |
| --- | --- |
| 19% Co/Al$_2$O$_3$ | 3.2 |
| 12% Co/TiO$_2$ | 0.5 |

The results show higher activity and productivity for cobalt/alumina v. cobalt/titania at relatively low pressure.

Example 6 - Comparative Performance of Al$_2$O$_3$ and TiO$_2$ Supported Co-Re at 1 atmosphere Examples as shown in European Patent Application 0 313 375.

| Catalyst | % CO Conversion |
| --- | --- |
| 12% Co/1% Re/Al$_2$O$_3$ | 33 |
| 12% Co/1% Re/TiO$_2$* | 17 |
| 12% Co/1% Re/TiO$_2$** | 17 |

*Support Calcined at 500° C.
**Support Calcined at 600° C.

Conditions: H$_2$ pretreatment at 1° C./minute to 350° C., hold for 10 hours, 2/1 H$_2$/CO, 1680 cm$^3$/g cat/hr feed rate, 10–30 hr on stream time.

These examples show a marked advantage for Co-Re/Al$_2$O over Co-Re/TiO$_2$ at low pressure. The data reported also show that the preferred catalyst Co-Re/TiO$_2$ is more active than Co-Re on supports such as chromia, zirconia, magnesia, silica-alumina, or silica.

Example 7 - Comparative Performance of Al$_2$O$_3$ and TiO$_2$ Supported Cobalt at 10 atmospheres These examples shown in Castier, D. et al ACS Publication 0097-6156/84, 0248-0039, Catalytic Materials, p. 39 (1984).

| Catalyst | % CO Conversion |
| --- | --- |
| 5% Co/Al$_2$O$_3$ | 17 |
| 5% Co/TiO$_2$ | 23 |

Conditions: H$_2$ pretreatment at 480° C. for 0.5 hours, 3/1 H$_2$/CO, 260° C. reaction temperature, 0.5 hours on stream time.

At ten atmospheres the advantage is reversed and Co/TiO$_2$ shows greater CO conversion than Co/Al$_2$O$_3$.

Example 8 - Comparative Performance of Al$_2$O$_3$ and TiO$_2$

Supported Co-Re Catalysts at 20 atmospheres
Example 7c and 7d are taken from U.S. Pat. No. 4,568,663, Table I; Examples 7a and 7b were run at 200° C., 20 psig. GHVS =1000, H$_2$/CO =2.0-2.15 and similarly as reported in U.S. Pat. No. 4,568,663.

| Catalyst | % CO Conversion |
| --- | --- |
| a) 12% Co/Al$_2$O$_3$ | 41 |
| b) 12% Co/0.5% Re/Al$_2$O$_3$ | 63 |
| c) 12% Co/TiO$_2$ | 65–75 |
| d) 12% Co/0.5% Re/TiO$_2$ | 80–85 |

Conditions: Calcination at 250° C., H$_2$ pretreatment as per Example 1 in U.S. Pat. No. 4,568,663, 2/1 H$_2$/CO, 1000 SHSV gas feed rate, 200° C. reaction temperature, >24 hours on stream time.

These examples again show the advantage reversed and Co-Re/TiO$_2$ is better at converting CO than Co-Re/Al$_2$O$_3$ at 20 atmospheres. However, because of greater surface area, the alumina catalysts can accept greater amounts of cobalt and rhenium, thereby considerably reducing the advantage.

What is claimed is:

1. A two stage hydrocarbon synthesis process comprising:
   (a) reacting in a first stage, hydrogen and carbon monoxide in the presence of a supported cobalt or ruthenium catalyst and obtaining a CO conversion to C$_2$+ hydrocarbons of at least 50% at reaction conditions including a pressure of at least 10 atmospheres;
   (b) recovering a reaction product comprising hydrogen and carbon monoxide and separating liquid therefrom;
   (c) reacting in a second stage, at a pressure below 10-12 atmospheres and no greater than the outlet pressure of the first stage, the remaining reaction products in the presence of a catalyst comprising catalytically effective amounts of cobalt supported on alumina at reaction conditions; and
   (d) wherein the second stage catalyst is at least as active for CO conversion to C$_2$+ hydrocarbons as the first stage catalyst at second stage reaction pressure.

2. The process of claim 1 wherein the second stage catalyst contains rhenium.

3. The process of claim 1 wherein the second stage conversion of CO to C$_2$+ hydrocarbons is at least about 50%.

4. The process of claim 1 wherein the first stage pressure is at least 13 atmospheres.

5. The process of claim 1 wherein the first stage catalyst comprises a metal selected from the group consisting of cobalt and ruthenium supported on a material selected from the group consisting of silica, alumina, silica-alumina, and titania.

6. A two-stage hydrocarbon synthesis process comprising:
   (a) reacting in a first stage hydrogen and carbon monoxide in the presence of a supported cobalt containing catalyst, converting at least about 50% of the CO to C$_2$+ hydrocarbons at reactions including a pressure of at least 15 atmospheres;
   recovering a reaction product comprising hydrogen and carbon monoxide and separating liquids therefrom;
   (c) reacting the remaining reaction products in a second stage at a pressure below about 10 atmospheres and no greater than the outlet pressure of the first stage, in the presence of a catalyst comprising catalytically effective amounts of cobalt, a rhenium promoter and an alumina support, covering at least about 50% of the CO to $C_2+$ hydrocarbons at reaction conditions, and (d) wherein the second stage catalyst is at least as active for CO conversion to $C_2+$ hydrocarbons as the first stage catalyst at second stage reaction pressure.

7. The process of claim 6 wherein the CO partial pressure at the second stage outlet is at least about 0.3 atmospheres.

8. The process of claim 6 wherein the second stage catalyst contains about 5 to 60 wt% cobalt and the rhenium:cobalt ratio is at least about 0.05:1.

9. The process of claim 6 wherein the first stage CO conversion is about 60-70%.

10. The process of claim 6 wherein the hydrogen:carbon monoxide ratio of the first stage is about 1.7:1 to about 2.1:1.

11. The process of claim 6 wherein the first stage catalyst contains a promoter selected from the group consisting of ruthenium, rhenium, hafnium and cerium.

12. The process of claim 11 wherein the promoter is rhenium.

13. The process of claim 1 wherein the second stage catalyst support is at least 50 wt% alumina.

14. The process of claim 6 wherein the second stage catalyst support is at least 70 wt% alumina.

15. The process of claim 1 wherein the second stage catalyst is more active for CO conversion to $C_2+$ hydrocarbons than the first stage catalyst at second stage operating pressure.

16. The process of claim 6 wherein the second stage catalyst is more active for CO conversion to $C_2+$ hydrocarbons than the first stage catalyst at second stage operating pressure.

* * * * *